United States Patent
Witkin

(10) Patent No.: US 7,335,633 B2
(45) Date of Patent: Feb. 26, 2008

(54) DETECTING RECURRENT VULVOVAGINAL CANDIDIASIS OR VULVAR VESTIBULITIS SYNDROME AND METHOD FOR TREATING SAME

(75) Inventor: Steven S. Witkin, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/032,981

(22) Filed: Jan. 11, 2005

(65) Prior Publication Data

US 2005/0191667 A1    Sep. 1, 2005

Related U.S. Application Data

(60) Provisional application No. 60/535,766, filed on Jan. 12, 2004.

(51) Int. Cl.
*A61K 38/16* (2006.01)
(52) U.S. Cl. .......................................................... 514/2
(58) Field of Classification Search ...................... None
See application file for complete search history.

(56) References Cited

U.S. PATENT DOCUMENTS

2004/0006009 A1* 1/2004 Larsen et al. .................. 514/8

FOREIGN PATENT DOCUMENTS

WO    WO 00/70043    11/2000

OTHER PUBLICATIONS

Babula et al., Clin. Infect. Dis., 2003, 37, 733-7.*
Neth et al., Infect. Imm., 2000, 68, 688-93.*
Medline Plus, Medical Encyclopedia, Vaginal yeast infection, http://www.nlm.nih.gov/medlineplus/ency/article/001511.htm.*
Metts, Am. Fam. Phys., 1999, 59, 1547, http://www.aafp.org/afp/990315ap/1547.htm, pp. 1-12.*
Helm, Am. Fam. Phys., 2001, 63, 1535-44.*
Pirotta et al. BMJ, 2004, 329, 7465-70.*
Valdimarsson et al., Scand. J. Immunol., 1998, 48, 116-23.*
Juliger, Simone, et al., "Restricted polymorphisms of the mannose-binding lectin gene in population of Papua New Guinea", *Mutation Research* 2002, 505:87-91.
Madsen, Hans O., et al., "Different Molecular Events Result in Low Protein Levels of Mannan-Binding Lectin in Populations from Southeast Africa and South Amercia", *The Journal of Immunology* 1998, 161:3169-3175.

* cited by examiner

*Primary Examiner*—Cecilia J. Tsang
*Assistant Examiner*—Christina M. Bradley
(74) *Attorney, Agent, or Firm*—Hoffmann & Baron, LLP; Irving N. Feit

(57) ABSTRACT

In one embodiment, the invention provides a method for detecting increased risk of vulvovaginal candidiasis or vulvur vestibulitis syndrome. The method comprises obtaining a biological sample and determining whether a mutant allele of mannose-binding lectin gene is present in the sample. In another embodiment, the invention provides a method for treating or preventing vulvovaginal candidiasis or vulvur vestibulitis syndrome in a female in need thereof. The method comprises administering an effective amount of a mannose-binding lectin protein.

10 Claims, 2 Drawing Sheets

US 7,335,633 B2

DETECTING RECURRENT VULVOVAGINAL CANDIDIASIS OR VULVAR VESTIBULITIS SYNDROME AND METHOD FOR TREATING SAME

This application asserts priority to U.S. Provisional Application No: 60/535,766 filed on Jan. 12, 2004, the specification of which is hereby incorporated by reference in its entirety.

BACKGROUND OF THE INVENTION

As the DNA sequences of the human genome are revealed, it is increasingly clear that many genes are polymorphic. In coding or noncoding regions of a specific gene, there may be either a single base pair substitution of one nucleotide for another, multiple base pair changes, or a variable number of repeats of a short, repetitive DNA sequence.

Polymorphic variations may influence the rate of gene transcription, the stability of the messenger RNA, or the quantity and activity of the resulting protein. Thus, the susceptibility or severity of a number of disorders or conditions may be influenced by possession of specific alleles of polymorphic genes.

An example of a polymorphic gene is the gene for mannose-binding lectin. Mannose-binding lectin (MBL) is a circulating protein, and a component of the innate immune defense system. The lectin binds to mannose, N-acetylglucosamine and fucose residues on the surface of microorganisms. Such binding results in complement activation.

In addition, macrophages and dendritic cells contain cell surface receptors that recognize MBL, facilitating opsonization of microorganisms with bound MBL on their surface (Babovic-Vuksanovic et al.,*Asthma Immunol.*, 1999; 82:134-43). Reduction in serum levels of MBL have been associated with opsonization defects (Super et al., *Lancet*, 1989; 2:1236-1239) and with an increased risk of recurrent infections in young children (Turner et al., *Clin. Exp. Immunol.*, 1991; 86:53-56 and Koch et al., *JAMA*, 2001; 285:1316-1321).

At least three alleles exist for the mannose-binding lectin gene. The wild type allele is called allele A. Genetic variants of the wild type allele are considered to be mutant alleles.

An example of a mutant allele of mannose-binding lectin is allele B, which is the most studied of the mutant alleles. In allele B, there is a single nucleotide substitution of an adenine for a guanine in codon 54 of exon 1. This substitution results in replacement of aspartic acid for glycine in the MBL protein. As a consequence of this alteration, the assembly of the mature MBL protein, including, for example, glycosylation, is inhibited, and its stability is markedly reduced (Sumiya et al., *Lancet*, 1991; 337:1569-1570 and Lipscombe et al., *Immunology*, 1995; 85:660-667).

The decrease in circulating MBL concentrations has been shown to correlate with possession of mutant alleles in exon 1 of MBL. Serum levels of MBL are approximately 1.2 to 1.7 µg/ml in individuals who are homozygous for allele A, 0.3 µg/ml in individuals who are heterozygous for allele A and B, and 10 ng/ml in individuals homozygous for allele B.

Vulvovaginal candidiasis is a yeast infection of the vulva and vagina. Millions of women worldwide suffer from vulvovaginal candidiasis. Women with recurrent vulvovaginal candidiasis experience frequent episodes of infection, which result in considerable morbidity and suffering.

Vulvar vestibulitis is a condition characterized by redness and pain of the vaginal vestibule and an inability to experience pain-free vaginal penetration. There is currently no known cause for vulvar vestibulitis. Many women with vulvar vestibulitis syndrome suffer physically and emotionally for months or years. These women typically see a number of physicians, and try many unsuccessful treatments in search of relief.

Several environmental factors have been identified which predispose women to recurrent vulvovaginal candidiasis or vulvar vestibulitis syndrome. These factors include pregnancy, oral contraceptives, exogenous hormones, antibiotics, diabetes mellitus, etc. However, the majority of women with recurrent vulvovaginal candidiasis or vulvar vestibulitis syndrome are not subjected to these predisposing factors.

Therefore, it would be beneficial to be able to identify females who are at risk for developing vulvovaginal candidiasis or vulvar vestibulitis syndrome. It would also be beneficial to be able to treat and/or prevent vulvovaginal candidiasis or vulvar vestibulitis syndrome.

SUMMARY OF THE INVENTION

Figure 1:
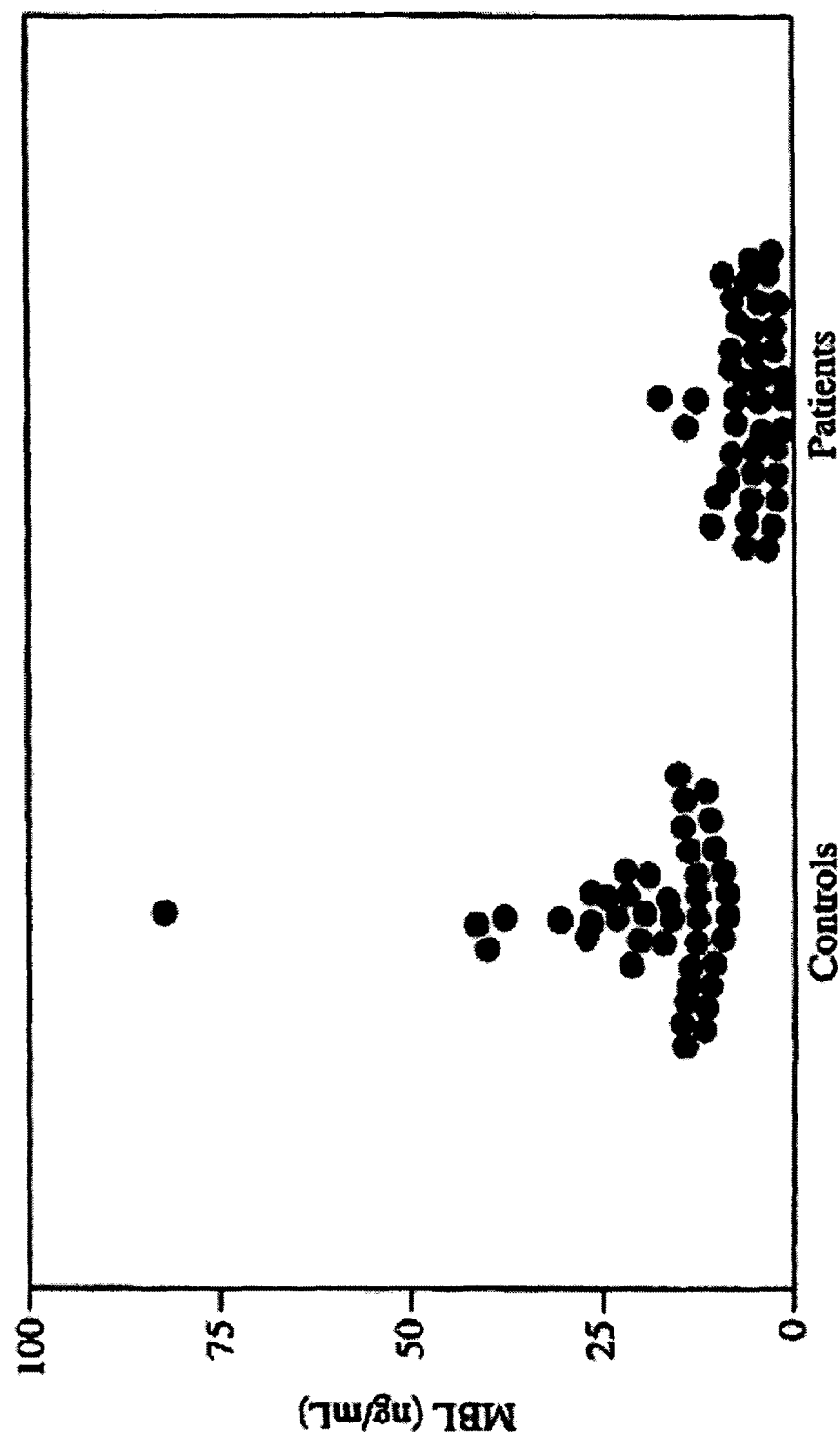
FIG. 1: Vaginal mannose-binding lectin (MBL) concentrations in women with recurrent vulvovaginal candidiasis (patients) and in control subjects (controls). MBL concentrations in vaginal lavage samples obtained from patients and controls were determined by ELISA.

The invention relates to a method for detecting increased risk of vulvovaginal candidiasis or vulvar vestibulitis syndrome in a human female. The method comprises obtaining a biological sample from the female and determining whether a mutant allele of mannose-binding lectin gene is present in the sample. The presence of a mutant allele indicates increased risk for vulvovaginal candidiasis or vulvar vestibulitis syndrome.

In another embodiment, the invention relates to a method for treating or preventing vulvovaginal candidiasis or vulvar vestibulitis syndrome in a human female in need thereof. The method comprises administering an effective amount of a mannose-binding lectin protein to the female.

DETAILED DESCRIPTION OF THE INVENTION

The invention is based on the surprising discovery by the inventor that the presence of a mutant allele of mannose-binding lectin gene is associated with an increased risk of vulvovaginal candidiasis or vulvar vestibulitis syndrome in human females. Vulvovaginal candidiasis and vulvar vestibulitis can occur in human females of all ages. For example, the female can be an infant, a girl, a teen-ager, or an adult.

Mannose-Binding Lectin Allele

In this specification, allele A is considered the wild-type allele for mannose-binding lectin gene. The nucleotide sequence for allele A can be found in Genbank under the accession number Y16577. The coding sequence (cds) for allele A in accession number Y16577 occurs from nucleotide position 892 to 1638. The nucleotide sequence for Genbank Accession number Y16577 is hereby incorporated by reference.

A mutant allele of mannose-binding lectin gene is typically any allele having a nucleotide sequence which is a genetic variant of allele A. Usually, the variation results in a change in the amino acid sequence of the wild-type mannose-binding lectin protein. The variation can occur in any one or more exons. For example, the variation can be in exon 1, 2, 3 or 4.

The variation can be any variation. For example, the variation can occur as a result of a single base pair substitution of one nucleotide for another, multiple base pair substitutions, additions or deletions, and combinations thereof.

Some examples of mutant alleles include alleles B, C and D. The nucleotide sequence for allele B can be found in Genbank under the accession number Y16579, and is incorporated by reference. The cds for allele B in accession number Y16579 occurs from nucleotide position 892 to 1638. As stated above, allele B has a single nucleotide substitution of an adenine for a guanine in codon 54. The substitution occurs in exon 1, and results in replacement of aspartic acid for glycine in the MBL protein.

The nucleotide sequence for allele C can be found in Genbank under accession number Y16578, and is incorporated by reference. The cds for allele C in accession number Y16578 occurs from nucleotide position 886 to 1632. Allele C has a single nucleotide substitution of an adenine for a guanine in codon 57. The substitution occurs in exon 1, and results in replacement of glycine by glutamic acid in the MBL protein.

The nucleotide sequence for allele D can be found in Genbank under accession number Y16582, and is incorporated by reference. The cds for allele D in accession number Y16582 occurs from nucleotide position 892 to 1638. Allele D has a single nucleotide substitution of thymine for cytosine in codon 52. The substitution occurs in exon 1, and results in replacement of arginine by cysteine.

Detecting Increased Risk for Vulvovaginal Candidiasis or Vulvar Vestibulitis Syndrome In one aspect, the invention relates to a method for detecting increased risk of vulvovaginal candidiasis or vulvar vestibulitis syndrome in a human female. "Increased risk" refers to a statistically higher frequency of occurrence of either condition in a female in comparison to the average frequency of occurrence. The frequency is typically increased by at least about 50%, more typically by at least about 75%, even more typically at least about 100%, and even at least about 200%. Usually, the average frequency of occurrence is about 5% for recurrent vulvovaginal candidiasis and about 5% for vulvar vestibulitis syndrome.

Vulvovaginal candidiasis (commonly called thrush) is a condition caused by a yeast infection of the vulva and vagina. The infection typically is accompanied by pain, inflammation, redness and soreness of the vulva and vaginal region.

The yeast responsible for vulvovaginal candidiasis is from the genus *Candida*. The yeast can be any species of *Candida*. Examples of *Candida* species include *C. albicans*, *C. tropicalis*, *C. parapsilosis*, *C. glabrata* amd *C. guilliermondii*. Typcially the *Candida* species is *C. albicans*.

Some females develop recurrent vulvovaginal candidiasis. In these females, the fungal infection generally persists despite adequate conventional therapy, or reappears shortly after cessation of treatment. Such conventional therapy and treatments include the use of anti-fungal creams. In this specification, vulvovaginal candidiasis includes recurrent vulvovaginal candidiasis.

Vulvar vestibulitis is a condition typically characterized by redness and pain of the vaginal vestibule. The condition generally causes inflammation of the skin, and of the mucous-secreting glands, of the vestibule. Vestibulitis occurs in the area around the opening of the vagina. Normally, vulvar vestibulitis is commonly seen in the lower part of this area. Currently, there is no known cause of vulvar vestibulitis.

The first step in the method for detecting increased risk is obtaining a biological sample. The biological sample can be any sample which contains DNA. Examples of biological samples include blood, salvia, cervicalvaginal fluid and epithelial cells.

The biological sample can be obtained by any method known to those in the art. Suitable methods include, for example, venous puncture of a vein to obtain a blood sample and cheek cell scraping to obtain a buccal sample.

DNA can be isolated from the biological sample by any method known to those in the art. For example, commercial kits, such as the QIAGEN System (QIAmp DNA Blood Midi Kit, Hilder, Germany) can be used to isolate DNA.

The DNA is optionally amplified by methods known in the art. One suitable method is the polymerase chain reaction (PCR) method described by Saiki et al., *Science* 239:487 (1988), U.S. Pat. No. 4,683,195 and Sambrook et al. (Eds.), Molecular Cloning, Third Edition, Cold Spring Harbor Laboratory Press, Cold Spring Harbor, N.Y. (2001). For example, oligonucleotide primers complementary to a nucleotide sequence flanking and/or present at the site of the mutation of the allele can be used to amplify the allele.

In the next step of the method, the isolated DNA is used to determine whether a mutant allele of mannose-binding lectin gene is present in the sample. The presence of a mutant allele indicates increased risk of vulvovaginal candidiasis or vulvar vestibulitis syndrome.

The presence of a mutant allele can be determined by any method known to those skilled in the art. Such methods include, for example, use of nucleic acid probes and polymerase chain reaction (PCR). Methods for making and using nucleic acid probes are well documented in the art. For example, see Keller G H and Manak M M, *DNA Probes*, $2^{nd}$ ed., Macmillan Publishers Ltd., England (1991) and Hames B D and Higgins S J, eds., *Gene Probes I* and *Gene Probes II*, IRL Press, Oxford (1995).

For example, methods for distinguishing wild-type DNA from mutants containing a single nucleotide change are described in PCT Application WO 87/07646. The methods disclosed in PCT Application WO 87/07646 are incorporated herein by reference.

Briefly, oligonucleotides containing either the wild-type or mutant sequence are hybridized under stringent conditions to dried agarose gels containing target RNA or DNA digested with appropriate restriction endonuclease. An example of a suitable stringent condition includes a temperature of two or more degrees below the calculated $T_m$ of a perfect duplex. The oligonucleotide probe hybridizes to the target DNA or RNA detectably better when the probe and the target are perfectly complementary.

A particularly convenient method for assaying a single point mutation by means of oligonucleotides is described in Segev, PCT Application WO 90/01069. The methods disclosed in PCT Application WO 90/01069 are hereby incorporated by reference.

Briefly, two oligonucleotide probes for each wild-type or mutated strand being assayed are prepared. Each oligonucleotide probe is complementary to a sequence that straddles the nucleotides at the site of the genetic variation. Thus, a gap is created between the two hybridized probes.

The gap is filled with a mixture of a polymerase, a ligase, and the nucleotide complementary to that at the position to form a ligated oligonucleotide product. Either of the oligonucleotides or the nucleotide filling the gap may be labelled by methods known in the art.

The ligated oligonucleotide product can be amplified by denaturing it from the target, hybridizing it to additional oligonucleotide complement pairs, and filling the gap again, this time with the complement of the nucleotide that filled the gap in the first step.

The oligonucleotide product can be separated by size and the label is detected by methods known in the art.

Mutations may also be detected if they create or abolish restriction sites; see Baker et al, Science 244, 217-221 (1989). Some additional examples of the use of restriction analysis to assay point mutations are given in Weinberg et al, U.S. Pat. No. 4,786,718 and Sands, M. S. and Birkenmeier, E. H., Proc. Natl. Acad. Sci. USA 90:6567-6571 (1993).

For example, point mutations can be detected by means of single-strand conformation analysis of polymerase chain reaction products (PCR-SSCP). This method is described in Orita, M. et al., Proc. Natl. Acad. Sci. USA 86:2766-2770 (1989), Suzuki, Y. et al., Oncogene 5:1037-1043 (1990), and Sarkar, F. H. et al., Diagn. Mol. Pathol. 4:266-273 (1995).

Some additional methods for distinguishing wild-type DNA and its mutants are described by De Ley et al., J. Bacteriol. 101:738-754 (1970); Wood et al., Proc. Natl. Acad. USA 82:1585-1588 (1985); Myers et al., Nature 313:495-497 (1985); and Myers et al., Science 230:1242-1246 (1985).]

The presence of a mutant allele of mannose-binding lectin indicates an increased risk of vulvovaginal candidiasis or vulvar vestibulitis syndrome. A human female at increased risk can be heterozygous or homozygous for a mutant allele. For example, the female can be heterogyzous for two different mutant alleles, heterozygous having one allele A and one mutant allele, or homozygous for the same mutant allele.

Methods of Treating or Preventing Vulvovaginal Candidiasis or Vulvar Vestibulitis Syndrome In another aspect, the invention relates to a method for treating or preventing vulvovaginal candidiasis or vulvar vestibulitis syndrome in a human female in need thereof. The method comprises administering an effective amount of a mannose-binding lectin protein.

The mannose-binding lectin protein can be any mannose-binding lectin protein or fragment thereof capable of binding to mannose, N-acetylglucosamine and/or fucose, and of treating or preventing vulvovaginal candidiasis of vulvar vestibulitis syndrome. Preferably, the mannose-binding lectin protein corresponds through the genetic code to the nucleotide sequence of allele A or a fragment of allele A.

The amino acid sequence of mannose-binding lectin protein deduced from allele A can be found in Genbank under accession number CAB56120. The amino acid sequence disclosed in Genbank Accession number CAB56120 is hereby incorporated by reference.

A "fragment of allele A" as defined herein refers to a portion of the entire nucleotide coding sequence (cds) of allele A. The fragment of allele A can be any length that encodes a sufficient fragment of mannose binding protein such that the protein fragment is functionally active and satisfies the criteria mentioned above. For example, the length of the fragment of allele A typically has a minimum nucleotide length of about 24 nucleotides, preferably about 75 nucleotides, more preferably about 200 nucleotides, even more preferably about 400 nucleotides, and most preferably about 600 nucleotides. The fragment of allele A also generally has at least about 10% identity, preferably about 25%, more preferably about 50%, even more preferably about 75%, and still more preferably about 90%, and most preferably about 95% identity to the nucleotide coding sequence of allele A.

The protein also can be a functional equivalent of the protein deduced from the nucleotide sequence of allele A. The protein is considered a functional equivalent if it has the same function as the protein deduced from the nucleotide sequence of allele A. Preferably the amino acid sequence has at least about 70%, more preferably at least 80%, even more preferably at least about 90%, and most preferably at least about 95% identity with the amino acid sequence deduced from the nucleotide sequence of allele A.

For example, the amino acid sequence of mannose-binding protein can be any amino acid sequence deduced from allele B, C or D.

Functional equivalents of mannose-binding lectin protein preferably include conservative amino acid substitutions. Amino acids may be grouped according to their physiochemical characteristics as follows:

(a) Non-polar amino acids: Ala(A) Ser(S) Thr(T) Pro(P) Gly(G);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W).

Substitutions of an amino acid in the protein by another amino acid in the same group is referred to as a conservative substitution and may preserve the physiochemical characteristics of the original peptide. In contrast, substitutions of an amino acid in a protein by another amino acid in a different group is generally more likely to alter the characteristics of the original protein.

The protein or fragments thereof may be prepared by methods known in the art. For example, the protein or fragment may be prepared by providing DNA that encodes the protein; amplifying or cloning the DNA in a suitable host; expressing the DNA in a suitable host; and harvesting the protein. These methods are known to those skilled in the art. See for example Sambrook et al. (2001). See also PCT international publication number WO 00/70043 to Thiel et al. which discloses a method for producing recombinant mannose-binding lectin protein.

Other methods include synthesizing the protein chemically from individual amino acids. Suitable methods for synthesizing the protein or fragments thereof are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997). Suitable methods for synthesizing DNA are described by Caruthers in Science 230:281-285 (1985) and DNA Structure, Part A: Synthesis and Physical Analysis of DNA, Lilley, D. M. J. and Dahlberg, J. E. (Eds.), Methods Enzymol., 211, Academic Press, Inc., New York (1992).

An effective amount of mannose-binding lectin protein in accordance with the methods of the present invention can be any amount that is effective in treating or preventing vulvovaginal candidiasis or vulvar vestibulitis syndrome. The effective amount can be determined during pre-clinical trials and clinical trials by methods familiar to physicians and clinicians. For example, an effective amount of mannose-binding lectin protein can be from about 0.1 mg to 10 mg.

Mannose-binding lectin protein can be administered to any human female in need thereof. Examples of females in need include, for example, females who are at increased risk of vulvovaginal candidiasis or vulvar vestibulitis syndrome, and those who are already suffering from vulvovaginal candidiasis or vulvar vestibulitis syndrome. Females who are at increased risk include females who are not homozygous for allele A, as well as those who have a history of vulvovaginal candidiasis or vulvar vestibulitis syndrome.

The mannose-binding lectin protein may be administered by any method known in the art. Some examples of suitable modes of administration include topical and systemic administration. Systemic administration is preferably parenteral. Parenteral administration of mannose-binding lectin protein include, for example intravenous, intramuscular, and subcutaneous injections.

For instance, mannose-binding lectin protein may be administered by sustained release, as is known in the art. Sustained release administration is a method of drug delivery to achieve a certain level of the drug over a particular period of time.

Typically, mannose-binding lectin protein is formulated in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The formulations may also comprise one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of mannose-binding lectin protein.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example sodium chloride, or sodium/potassium phosphate, respectively. Preferably, the buffering agent maintains the pH of the formulation in the range of about 5.5 to about 7.5. The salt and/or buffering agent is also useful to maintain the osmolality at a level suitable for administration. Preferably the salt or buffering agent is present at a roughly isotonic concentration of about 150 mM to about 300 mM.

The formulations may further contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as for example a morphine derivative; or an isotonic agent etc., such as described above. As a further precaution against oxidation or other spoilage, the mannose-binding lectin protein formulations may be stored under nitrogen gas in vials sealed with impermeable stoppers.

EXAMPLES

Example 1

Materials and Methods for Vulvovaginal Candidiasis Study

The study population consisted of 42 women (age, 18-35 years) who had four or more culture-verified symptomatic episodes of a vulvovaginal *Candida* infection during a 12-month period and who currently had symptoms consistent with a vaginal *Candida* infection (i.e., pruritis, burning, and abnormal discharge) and a positive *Candida* culture. Control subjects were 43 women who had no current gynecologic complaints, who had no history of vaginal *Candida* infection, and who were currently culture-negative for pathogens. All patients and control subjects were seen at the outpatient obstetrics/gynecology department of Riga First Hospital in Riga, Latvia. Patients and control subjects were matched for age, socioeconomic and marital status, and number of children. All were ethnic Latvians. Exclusion criteria for this study were pregnancy, diabetes, known immunodeficiencies, use of immunosuppressive medications, or history of hysterectomy.

Informed consent was obtained from all subjects, and the guidelines for human experimentation of the US Department of Health and Human Services and Riga Stradin's University were followed in the conduct of clinical research.

Cervicovaginal samples were obtained by instilling 3 ml of sterile saline into the posterior vaginal fornix, mixing with a cotton swab, and then withdrawing the solution with a syringe. An aliquot of each sample was cultured for *Candida* species on Sabouraud's medium and speciated by culture on CHROM agar (CHROM Agar Candida Co.). Samples were also tested for *Trichomonas vaginalis*, by wet mount; *Chlamydia trachomatis*, by PCR; *Neisseria gonorrhoeae*, by culture; HIV, by antibody testing; and bacterial vaginosis, using the Amsel criteria (Amsel et al., *Am. J. Med,* 1983; 74:14-22). The samples were centrifuged to obtain supernatant and pellet fractions that were immediately frozen at −20° C. Frozen samples were shipped to the Division of Immunology and Infectious Diseases, Department of Obstetrics and Gynecology, Cornell (New York) on dry ice for analysis.

The vaginal concentrations of MBL were determined using a commercial ELISA (Cell Sciences) with a 1 to 5 dilution of the supernatant fractions. The lower limit of sensitivity was 3.1 ng/mL.

DNA was extracted from the pellet fractions as described elsewhere (Genc et al., *J. Obstet. Gynecol.,* 2002; 187:157-163). In brief, the pellets were thawed, washed, and resuspended in a 1% solution of the nonionic detergent, Brij 35 in Tris buffer containing 5 mg/ml proteinase K. Cells were lysed by incubation at 56° C. for 60 min, and the proteinase K was then inactivated by increasing the temperature to 95° C. for 10 min. The lysed samples were diluted 1 to 5 in 10 mmol/l Tris-HCl that contained 1.5 mmol/l of $MgCl_2$; 50 mmol/l of KCl; 0.2 mmol/l each of deoxyadenosine triphosphate, deoxyctidine triphosphate, deoxyguanosine triphosphate, and thymidine triphosphate; 1.25 units of Taq DNA polymerase; and 30 pmol of oligonucleotide primers that amplified the codon 54 polymorphic region of the MBL gene (Madsen et al., *Immunogenetics,* 1994; 40:37-44). The final volume was 0.05 ml. Samples were incubated in a thermal cycler for 2 min at 94° C., followed by 35 cycles of 94° C. for 50 s, 58° C. for 1.5 min, and 72° C. for 15 s. Lastly, the samples were incubated at 72° C. for 5 min.

The PCR amplicons were then digested by incubation at 37° C. for 18 h with Ban I endonuclease (New England BioLabs) in buffer provided by the manufacturer. Fragments were analyzed on 2% agarose gels and stained with ethidium bromide. Ban I digestion resulted in either formation of two 260 and 89 bp fractions (wild-type; allele A) or a single uncut 349 bp fraction (mutant; allele B).

The relationship between genotype frequencies and diagnosis was analyzed by Fisher's exact test. Differences in median MBL concentrations between patients and control subjects were analyzed using the Mann-Whitney U test. The relation between vaginal MBL levels and MBL genotype was analyzed by 1-way analysis of variance and Tukey-Kramer multiple comparisons test. $P<0.05$ was considered to be statistically significant.

Example 2

Demographic and Clinical Characteristics of Patients and Control Subjects

Demographic and clinical characteristics of patients and control subjects are detailed in Table 1 below. *Candida albicans* was detected in 38 (90.5%) of the patients with RVVC, *Candida tropicalis* was detected in 3 (7.1%), and *Candida krusei* was detected in 1 (2.4%). Among the control women, 4 cultures (9.3%) were positive for *C. albicans*. No other *Candida* species were detected in the control subjects. Ten patients with RVVC and none of the control subjects were positive for bacterial vaginosis. All patients and control subjects tested negative for *T. vaginalis, C. trachomatis, N. gonorrhoea*, and HIV.

TABLE 1

Demographic and Clinical Characteristics of Patients with Recurrent Vulvovaginal Candidiasis (RVVC) and Control Subjects.

| Characteristic | Patients with RVVC (n = 42) | Control subjects (n = 43) |
|---|---|---|
| Age, mean years (range) | 26.8 (18-35) | 25.4 (18-35) |
| University education | 21 (50) | 16 (37.2) |
| Salary <$200 a month, % of subjects | 38.1 | 60.5 |
| Age at first sexual intercourse, mean years | 19.6 | 18.4 |
| Married | 20 (47.6) | 20 (46.5) |
| Smoker | 12 (28.6) | 9 (20.9) |
| Vaginal or vulvar erythema present | 29 (69.0) | 0 |
| Abnormal vaginal discharge present | 31 (73.8) | 0 |
| Vaginal fissures and/or excoriations present | 24 (57.1) | 0 |
| Mean no. of pregnancies | 2.4 | 2.3 |
| Mean no. of children | 1.1 | 1.0 |
| History of spontaneous abortion | 24 (57.1) | 23 (53.5) |
| *Candida* infection | | |
| *C. albicans* | 38 (90.5) | 4 (9.3) |
| *C. tropicalis* | 3 (7.1) | 0 |
| *C. krusei* | 1 (2.4) | 0 |
| Bacterial vaginosis | 10 (23.8) | 0 |

NOTE.
Data are no. (%) of subjects, unless otherwise indicated.

Example 3

Women with RVVC have Decreased Concentrations of MBL

The distribution of vaginal MBL protein concentrations in patients with RVVC and control subjects is shown in FIG. 1. The median MBL concentration in control subjects was 15.9 ng/mL (range, 10.1-84.1 ng/ml), compared with 7.3 ng/mL (range, 2.9-18.7 ng/ml) for women with RVVC ($P<0.0001$).

Example 3

Recurrent Vulvovaginal Candidiasis is Associated with a Gene Polymorphism in Mannose-Binding Lectin The distribution of MBL alleles was significantly different in control subjects and patients with RVVC($P<0.0001$; table 2). More than 90% of the control subjects were homozygous for the wild-type allele (allele A), as opposed to only 31% of patients with RVVC. Conversely, almost 62% of patients with RVVC were allele A/allele B heterozygotes, compared with only 9.3% of control subjects. The frequency of allele B was 38.1% in patients with RVVC, as opposed to 4.7% in control subjects ($P<0.0001$). Sixty-eight percent of the patients who were culture-positive for *C. albicans* were either allele B heterozygotes or homozygotes, 100% of the women positive for *C. tropicalis* were allele B heterozygotes, and the single woman with *C. krusei* infection was allele A homozygous.

TABLE 2

Relation Between Mannose-binding Lectin (MBL) Gene Polymorphism and Recurrent Vulvovaginal Candidiasis (RVVC).

| | No. (%) of subjects | |
|---|---|---|
| MBL genotype | RVVC group (n = 42) | Control group (n = 43) |
| AA | 13 (31.0)[a] | 39 (90.7) |
| AB | 26 (61.9)[b] | 4 (9.3) |
| BB | 3 (7.1) | 0 (0) |

[a]$P < 0.0001$,
[b]$P < 0.0001$

Although the number of subjects is small, there was no relationship between bacterial vaginosis and MBL genotype. Allele A homozygotes, allele A/B heterozygotes, and allele B homozygotes were present in 30%, 50%, and 20% of the patients with bacterial vaginosis, respectively.

Example 4

Decreased MBL Concentrations is Associated with Possession of Allele B

Figure 2:
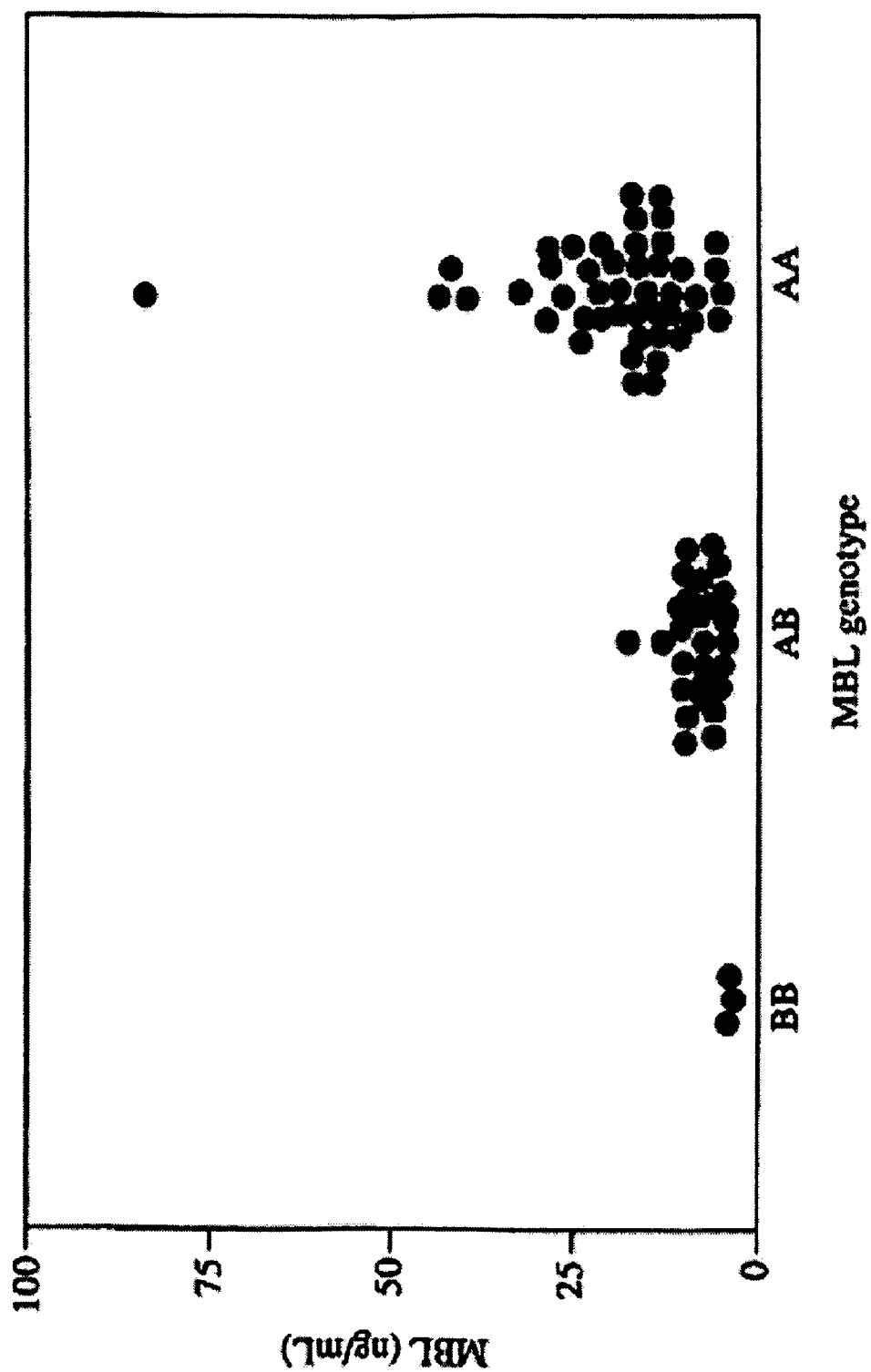
FIG. 2: Relation between mannose-binding lectin (MBL) genotype and MBL concentrations in the vagina. A single base pair substitution in codon 54 of the MBL gene in women with recurrent vulvovaginal candidiasis and in control subjects was determined by PCR and endonuclease digestion using primer pairs that spanned the polymorphic region. Vaginal MBL levels in patients and control subjects were determined by ELISA.

The relationship between vaginal MBL concentrations and MBL genotypes is shown in FIG. 2. The median MBL level in women who were allele A homozygous was 15.6 ng/ml (range, 4.2-84.1 ng/ml). This was significantly greater than the median level of 7.6 ng/ml (range, 4.5-17.3 ng/ml) in the A/B heterozygotes and 2.9 ng/ml (range, 2.9-3.6ng/ml) in the B/B homozygotes ($P<0.0001$).

Example 5

Materials and Methods for Vulvar Vestibulitis Syndrome

The study population consisted of 62 women from New York City and 60 women from Umea and Sundsvall, Sweden with strictly defined vulvar vestibulitis syndrome. All the subjects were white. Exclusion critieria were age<18 years, pregnancy or the presence of a mental disorder. The study was approved by the Institutional Review Boards of the participating hospitals.

Epithelial cells were obtained from the buccal cavity with a cotton swab (Epicentre, Madison, Wis.) and stored at 4° C. Samples from Sweden were shipped to New York by overnight express mail at room temperature. The epithelial cells were processed to release cellular DNA and stored at −80° C. until tested. Blood was obtained by venipuncture into heparinized tubes from the New York patients and stored at −80° C.

The lysed epithelial cells were diluted 1:5 and admixed with primer-pairs that spanned the codon 54 polymorphic region (Madsen et al., *Immunogenetics*, 1994; 40:37-44) in the presence of Taq DNA polymerase and all components needed for gene amplification (Babula et al., *Clin. Infect. Dis.*, 2003; 37:733-737). The samples, in a final volume of 0.05 ml, were incubated in a thermal cycler for 2 minutes at 94° C., followed by 35 cycles of 94° C. for 50 seconds, 58° C. for 90 seconds and 72° C. for 15 seconds. The final cycle was for 5 minutes at 72° C. PCR products were subsequently digested with BanI endonuclease (New England Biolabs) at 37° C. for 18 hours in buffer provided by the manufacturer. The final fragments were analyzed on 2% agarose gels following ethidium bromide staining. The wild-type allele (allele A, MBL*A) is digested by BanI into two 260 and 89 base pair fragments while the variant allele B (MBL*B) remains as a single 349 uncut base pair band.

The thawed plasma samples were diluted 1:100 and assayed for MBL concentration by a commercial ELISA kit (ANTIBODYSHOP, Gentofte, Denmark). Values were converted to ng/ml by reference to a standard curve generated in parallel to the test samples.

Genotype and allele frequencies were determined by direct counting and then dividing by the number of chromosomes to obtain allele frequency and by the number of women to obtain genotype frequency. Fisher's exact test was used to assess the differences in genotype distribution or alleles between patients and controls. The relation between MBL genotype and plasma MBL concentration was analyzed by 1-way analysis of variance and Tukey-Kramer multiple comparisons test. Goodness of fit to Hardy-Weinberg equilibrium was determined by comparing the expected genotype frequencies with the observed values, using the chi square test. A p value<0.05 was considered significant.

Example 6

Distribution of MBL Alleles in Vulvur Vestibulitis Patients and Controls

The distribution of MBL genotypes and alleles in vulvar vestibulitis patients and controls is shown in Table 3. 12.5% or 9.8% of the control women in New York or Sweden, respectively, were MBL*A/MBL*B heterozygotes. The remainder of these groups were MBL*A homozygotes.

In contrast, 35.5% of the New York patients (P=0.007) and 25.0% of the Swedish patients (P=0.02) with vulvar vestibulitis syndrome were MBL*A/MBL*B heterozygotes. Similarly, a total of 6.3% and 4.9% of the New York and Swedish controls were positive for the MBL*B allele as opposed to 17.7% (P=0.01) and 14.2% (P=0.02) of the New York and Swedish patients. The observed genotypes from each subject group were in Hardy-Weinberg equilibrium.

TABLE 3

Mannose-binding lectin gene polymorphism and vulvar vestibulitis syndrome in American and Swedish women

| | No. (%) positive | | | |
|---|---|---|---|---|
| | American | | Swedish | |
| Genotype or allele | VVS N = 62 | Control N = 48 | VVS N = 60 | Control N = 51 |
| A,A | 40 (64.5) | 42 (87.5) | 44 (73.3) | 46 (90.2) |
| A, B | 22 (35.5)[a] | 6 (12.5) | 15 (25.0)[c] | 5 (9.8) |
| B, B | 0 | 0 | 1 (1.7) | 0 |
| allele A | 102 | 90 | 103 | 97 |
| allele B | 22 (17.7)[b] | 6 (6.3) | 17 (14.2)[d] | 5 (4.9) |

[a]p = .007 vs. control, odds ratio (OR) = 3.850, 95% confidence interval (CI) = 1.414, 10.480
[b]p = .01 vs. control, OR = 3.235, 95% CI = 1.256, 8.335
[c]p = .02 vs. control, OR = 3.345, 95% CI = 1.129, 9.912
[d]p = .02 vs. control, OR = 3.202, 95% CI = 1.137, 9.011

Example 7

Plasma MBL Concentrations in Vulvar Vestibulitis Patients and Controls

The plasma MBL concentrations in vulvar vestibulitis patients and controls and their relationship to MBL genotype is shown in Table 4. There were no significant differences in MBL concentrations between patient and control MBL*A homozygotes or between patient and control MBL*A/MBL*B heterozygotes. However, in both patient and control groups the MBL concentration is more than 5 times higher in MBL*A homozygotes as in the MBL*A/MBL*B heterozygotes.

TABLE 4

Relationship between MBL genotype and plasma MBL concentration in American women

| Group tested | Genotype | Median ng/ml MBL (range) | p value |
|---|---|---|---|
| VVS + controls | A, A | 1980.5 (126-7161) | |
| | A, B | 278.0 (0.0-568.0) | p < ,.0001 |
| Controls | A, A | 2683 (687-7161) | |
| | A, B | 155.0 (0.0-425.0) | p < .0001 |
| VVS | A, A | 1593.0 (126-6818) | |
| | A, B | 284.0 (0.0-568.0) | p < .0001 |

Example 8

MBL Genotype and Vulvar Vestibulitis Syndrome Patient Characteristics

The relationship between MBL genotype and patient characteristics is shown in Table 5. vulvur vestibulitis syndrome patients who were MBL*A/MBL*B heterozygotes did not differ from patients who were MBL*A homozygotes in any parameter examined. Some of the New York patients were previously tested for the IL-1ra gene polymorphism. These was no relationship between MBL*B carriage and any IL-1ra genotype of allele.

TABLE 5

Relationship between mannose-binding lectin gene polymorphism and clinical data in women with vulvar vestibulitis syndrome.

| Parameter | American | | Swedish | |
| --- | --- | --- | --- | --- |
| | MBL AA (n = 35) | MBL AB (n = 22) | MBL AA (n = 44) | MBL AB (n = 15) |
| Median Age (range) | 30.5 (21-52) | 29.5 (23-47) | 23.5 (18-36) | 23.5 (19-37) |
| Age at symptom onset | 24.5 (10-46) | 25.0 (13-45) | 19.0 (15-25) | 19.5 (15-27) |
| Years with symptoms | 3.0 (0.3-17) | 4.0 (0.3-21) | 3.5 (1-18) | 2.0 (1-17) |
| Primary VVS | 17.6% | 17.6% | 26.8% | 50.0% |
| Secondary VVS | 82.4% | 82.4% | 73.2% | 50.0% |
| Hx of RVVC* | 47.1% | 23.5% | ND | ND |
| Hx of HPV* | 23.5% | 5.9% | ND | ND |
| Vaginal discharge | 67.6% | 35.3% | ND | ND |
| Pain on urination | 26.5% | 27.8% | ND | ND |
| Percent with children | 32.5% | 16.7% | 7% | 9% |

HX, History;
ND, not determined.
*Self reported.

What is claimed is:

1. A method for treating vulvovaginal candidiasis in a human female having a mutant allele of a mannose-binding lectin gene and/or a vaginal level of mannose-binding lectin protein from 2.9 to 18.7 ng/mL, the method comprising administering an effective amount of a wild-type mannose-binding lectin protein to the female.

2. A method according to claim 1, wherein the human female has a mutant allele, and the mutant allele is allele B.

3. A method according to claim 1, wherein the human female has a mutant allele, and the mutant allele is allele C.

4. A method according to claim 1, wherein the human female has a mutant allele, and the mutant allele is allele D.

5. A method according to claim 1, wherein the vulvovaginal candidiasis is recurrent vulvovaginal candidiasis.

6. A method according to claim 1, wherein the mannose binding lectin protein is administered topically.

7. A method according to claim 1, wherein the mannose binding lectin protein is administered systemically.

8. A method according to claim 1, wherein the female has a mutant allele of a mannose-binding lectin gene and a vaginal level of mannose-binding lectin protein from 2.9 ng/mL to 18.7 ng/mL.

9. A method for treating vulvovaginal candidiasis in a human female in need thereof having a mutant allele of a mannose-binding lectin gene and/or a serum level of mannose-binding lectin protein approximately 0.3 µg/mL or less, the method comprising administering an effective amount of wild-type a mannose-binding lectin protein to the female.

10. A method according to claim 9, wherein the female has a mutant allele of a mannose-binding lectin gene and a serum level of mannose-binding lectin protein approximately 0.3 µg/mL or less.

* * * * *